(12) United States Patent
Stoyanov

(10) Patent No.: US 12,387,005 B2
(45) Date of Patent: Aug. 12, 2025

(54) DE-IDENTIFYING DATA OBTAINED FROM MICROPHONES

(71) Applicant: DIGITAL SURGERY LIMITED, London (GB)

(72) Inventor: Danail V. Stoyanov, London (GB)

(73) Assignee: DIGITAL SURGERY LIMITED, London (GB)

( * ) Notice: Subject to any disclaimer, the term of this patent is extended or adjusted under 35 U.S.C. 154(b) by 239 days.

(21) Appl. No.: 18/124,633

(22) Filed: Mar. 22, 2023

(65) Prior Publication Data
US 2023/0315905 A1    Oct. 5, 2023

Related U.S. Application Data

(60) Provisional application No. 63/326,967, filed on Apr. 4, 2022.

(51) Int. Cl.
G06F 21/62    (2013.01)
G06V 20/40    (2022.01)

(52) U.S. Cl.
CPC .......... *G06F 21/6254* (2013.01); *G06V 20/44* (2022.01)

(58) Field of Classification Search
CPC .............................. G06F 21/6254; G06V 20/44
See application file for complete search history.

(56) References Cited

U.S. PATENT DOCUMENTS

| | | |
|---|---|---|
| 10,028,794 B2 | 7/2018 | Cagle et al. |
| 11,134,975 B2 | 10/2021 | Nicolaescu et al. |
| 12,039,998 B1 * | 7/2024 | Kao ......................... G10L 25/21 |
| 12,051,419 B1 * | 7/2024 | Wang ...................... G06F 40/211 |
| 12,067,482 B1 * | 8/2024 | Perumalla ............ G06F 18/2193 |
| 12,112,752 B1 * | 10/2024 | Gupta ...................... G10L 15/08 |
| 12,117,838 B1 * | 10/2024 | Sigurdsson ............. G10L 15/22 |
| 12,181,847 B1 * | 12/2024 | Brett ..................... G05B 19/042 |
| 12,190,877 B1 * | 1/2025 | Barber ................... H04R 1/406 |
| 2019/0252052 A1 | 8/2019 | Von Reden |
| 2019/0341050 A1 | 11/2019 | Diamant et al. |
| 2021/0012032 A1 * | 1/2021 | Bishop .................. H04L 67/125 |
| 2021/0169559 A1 | 6/2021 | Li et al. |

(Continued)

FOREIGN PATENT DOCUMENTS

WO    2021216566 A1    10/2021

OTHER PUBLICATIONS

Mendels, Custom NLP Approaches to Data Anonymization, 2020, Towards Data Science, p. 1-17 (Year: 2020).*

(Continued)

*Primary Examiner* — Stephen T Gundry
(74) *Attorney, Agent, or Firm* — CANTOR COLBURN LLP

(57) ABSTRACT

An aspect includes a computer-implemented method that de-identifies data received from microphones. The method includes receiving data from one or more microphones and de-identifying the data. The de-identifying includes inputting the data into a machine learning system that has been trained to detect patterns in the data that are likely to identify a specific entity, and to remove the detected patterns from the data to generate de-identified data. An output from the machine learning system is received, where the output includes the de-identified data. According to some aspects, the microphones can be located in an operating room.

19 Claims, 8 Drawing Sheets

(56) References Cited

U.S. PATENT DOCUMENTS

| | | | | |
|---|---|---|---|---|
| 2023/0134195 | A1* | 5/2023 | Hawkins | G16H 20/40 |
| | | | | 386/241 |
| 2024/0206989 | A1* | 6/2024 | Luengo Muntion | G06N 3/045 |
| 2024/0252263 | A1* | 8/2024 | Robu | A61B 90/37 |
| 2024/0296838 | A1* | 9/2024 | Ramakrishna | G06N 3/0455 |
| 2024/0299105 | A1* | 9/2024 | Roh | G06V 10/40 |
| 2024/0303984 | A1* | 9/2024 | Sanchez-Matilla | |
| | | | | G06V 10/774 |
| 2024/0331354 | A1* | 10/2024 | Azad | G06V 10/764 |
| 2024/0387031 | A1* | 11/2024 | Grantcharov | G16H 40/67 |
| 2024/0390103 | A1* | 11/2024 | Wolf | G16H 20/40 |
| 2024/0395287 | A1* | 11/2024 | Gras | G06T 11/60 |
| 2024/0403625 | A1* | 12/2024 | Vogler | G06N 3/0455 |
| 2024/0414135 | A1* | 12/2024 | Neumann | A61B 5/14532 |
| 2024/0428956 | A1* | 12/2024 | Stoyanov | G06V 20/48 |
| 2025/0014717 | A1* | 1/2025 | Stoyanov | G16H 40/00 |

OTHER PUBLICATIONS

Mendels Omri, "Custom NPL Approaches to Data Anonymization"; Feb. 6, 2023; 5 pages.
Extended European Search Report for Application No. 23165161.3; Jun. 15, 2023; 18 pages.
Nadja Jurgens, "The Blue; Blog. Immerse yourself in AI"; Jan. 6, 2023; 18 pages.

* cited by examiner

DE-IDENTIFYING DATA OBTAINED FROM MICROPHONES

CROSS-REFERENCE TO RELATED APPLICATIONS

This application claims the benefit of U.S. Provisional Application No. 63/326,967, filed Apr. 4, 2022, the disclosure of which is incorporated herein by reference in its entirety.

BACKGROUND

The present disclosure relates in general to computing technology and relates more particularly to computing technology for de-identifying data obtained from microphones.

Computer-assisted systems, particularly computer-assisted surgery (CAS) systems, can rely on video data digitally captured during a surgery in an operating room. Such video data can be stored and/or streamed. In some cases, the video data can be used within a system to augment a person's physical sensing, perception, and reaction capabilities. For example, such systems can effectively provide the information corresponding to an expanded field of vision, both temporal and spatial, that enables a person to adjust current and future actions based on the part of an environment not included in his or her physical field of view. Alternatively, or in addition, the video data, which can include or be accompanied by audio data captured by one or more microphones, can be stored and/or transmitted for several purposes such as archival, operational notes, training, post-surgery analysis, and/or patient consultation.

SUMMARY

According to an aspect, a computer-implemented method de-identifies data received from microphones. The method includes receiving data from one or more microphones and de-identifying the data. The de-identifying includes inputting the data into a machine learning system that has been trained to detect patterns in the data that are likely to identify a specific entity, and to remove the detected patterns from the data to generate de-identified data. An output from the machine learning system is received, where the output includes the de-identified data. According to some aspects, the microphones can be located in an operating room.

According to an aspect, a computer program product includes a memory device having computer executable instructions stored thereon, which when executed by one or more processors cause the one or more processors to perform operations including receiving labeled training data comprising a plurality of sets of phrases, each set of phrases including a phrase and a corresponding de-identified phrase. The operations also include generating, using the labeled training data, a machine learning model to detect patterns in input data that are likely to identify a specific entity and to remove the detected patterns from the data.

According to another aspect, a system includes a data collection system configured to capture a video of a surgical procedure, the video can include adjunct data received from one or more microphones. The system also includes a machine learning execution system configured to execute one or more machine-learning models to identify a plurality of surgical phases in the video and to de-identify the data received from the one or more microphones. The system further includes an output generator configured to store the video with the surgical phases identified and the de-identified data.

Additional technical features and benefits are realized through the techniques of the present invention. Aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the aspects of the invention are apparent from the following detailed description taken in conjunction with the accompanying drawings in which:

Figure 1:
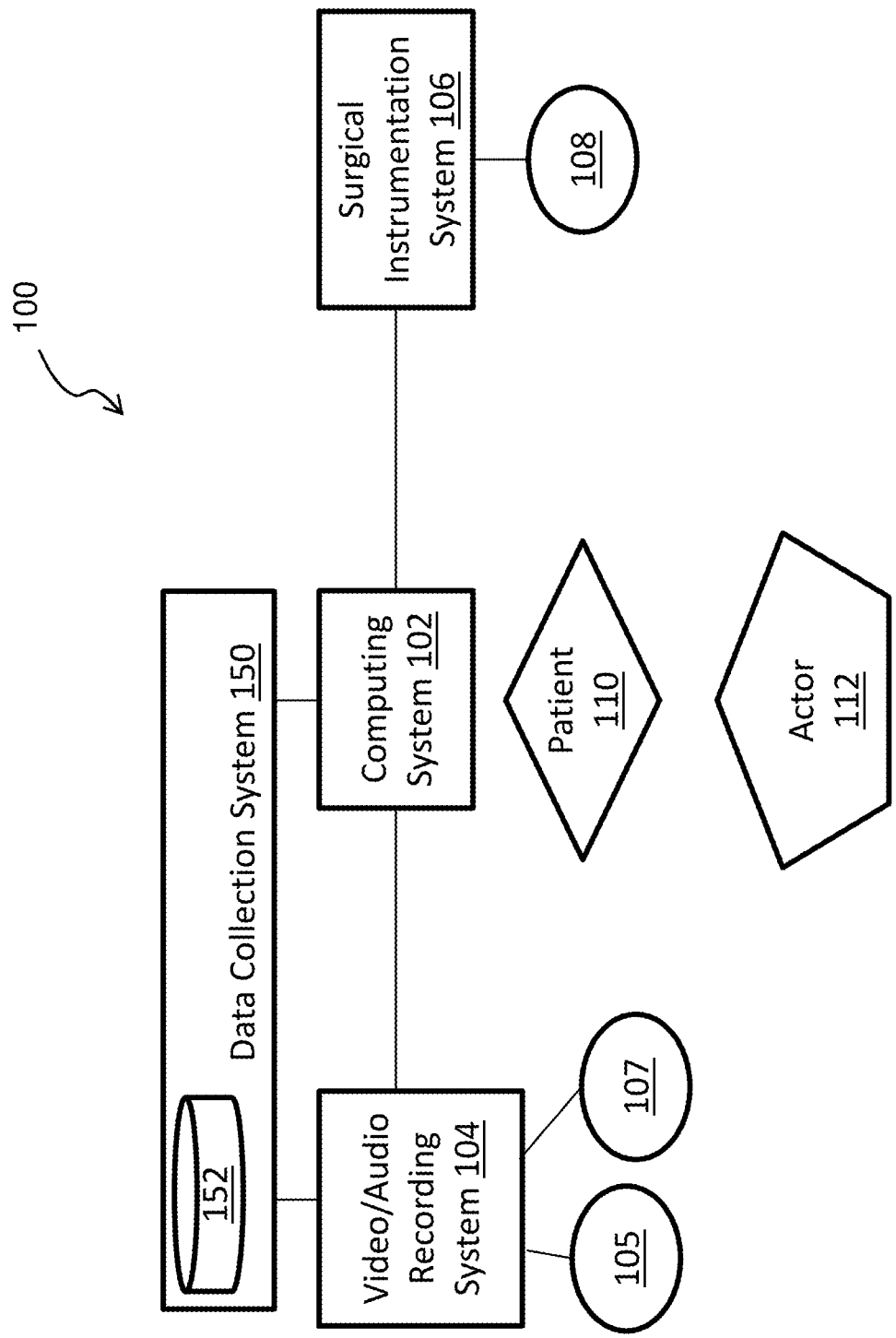
FIG. 1 depicts a computer-assisted surgery (CAS) system according to one or more aspects.

The diagrams depicted herein are illustrative. There can be many variations to the diagrams and/or the operations described herein without departing from the spirit of the invention. For instance, the actions can be performed in a differing order, or actions can be added, deleted, or modified. Also, the term "coupled" and variations thereof describe having a communications path between two elements and do not imply a direct connection between the elements with no intervening elements/connections between them. All of these variations are considered a part of the specification.

DETAILED DESCRIPTION

Exemplary aspects of the technical solutions described herein include systems and methods for de-identifying data that is captured by microphones located in operating rooms during surgical procedures. Audio data captured by one or more microphones during a surgical procedure can be used to provide valuable insight into the surgical procedure. Pairing the audio data with video, or image, data can provide additional information into the events that occurred and/or decisions that were made during the surgical procedure. To preserve patient privacy, data captured during a surgical procedure that is used for training or other purposes not related to the care of a specific patient should have any portions of the data that identify the specific patient removed or anonymized prior to being shared. It can also be desirable to remove or anonymize portions of the data that identify a specific health care provider or individual in the operating room. One or more aspects of the present invention include systems and methods that de-identify audio data by removing or anonymizing data that identifies a specific person, place, or company such as, but not limited to: a patient, a health care professional, a hospital, and/or the brand name of equipment in the operating room.

An operating room may contain a microphone located on a central console and/or one or more microphones affixed (e.g., via a clip or other means) to medical personnel or objects in the operating room. In addition, or alternatively, one or more microphones can be attached or integrated into one or more devices in the operating room such as, but not limited to surgical tools, video recorders, cameras, goggles, personal computers, smart watches, and/or smart phones.

Data de-identification can be used to preserve privacy by modifying data to prevent someone's personal identity from being revealed. De-identification can include breaking any link between the data and a specific entity (e.g., patient, medical provider, hospital, manufacturer of equipment) with whom the data is initially associated, including removing or transforming any data that might identify the entity. Types of information that can be removed or modified from audio data can include, but are not limited to: names of patients or surgeons or hospitals; medical record numbers; dates; surgical instrument manufacturers or model numbers; and/or phrases or language attributable to a particular person or subset of people.

Audio data is typically not recorded in the operating room today and if recorded it is handled by individuals without addressing the importance of anonymization. One or more aspects of the invention described herein capture important data from the operating room while complying with privacy requirements through de-identification of the data. The captured data can include, but is not limited to audio data, and the captured data can link to other operating room data sources.

In exemplary aspects of the technical solutions described herein, surgical data that is captured by a computer-assisted surgical (CAS) system is input to the analysis described herein to de-identify data that is captured by microphones located, for example, in operating rooms during surgical procedures.

Turning now to FIG. 1, an example CAS system 100 is generally shown in accordance with one or more aspects. The CAS system 100 includes at least a computing system 102, a video/audio recording system 104, and a surgical instrumentation system 106. As illustrated in FIG. 1, an actor 112 can be medical personnel that uses the CAS system 100 to perform a surgical procedure on a patient 110. Medical personnel, or health care professionals, can be a surgeon, assistant, nurse, administrator, or any other actor that interacts with the CAS system 100 in a surgical environment. The surgical procedure can be any type of surgery, such as but not limited to open or laparoscopic hernia repair, laparoscopic cholecystectomy, robotic laparoscopic surgery, or any other surgical procedure with or without a robot. In other examples, actor 112 can be a surgeon, anesthesiologist, theatre nurse, technician, an administrator, an engineer, or any other such personnel that interacts with the CAS system 100. For example, actor 112 can record data from the CAS system 100, configure/update one or more attributes of the CAS system 100, review past performance of the CAS system 100, repair the CAS system 100, etc.

A surgical procedure can include multiple phases, and each phase can include one or more surgical actions. A "surgical action" can include an incision, a compression, a stapling, a clipping, a suturing, a cauterization, a sealing, or any other such actions performed to complete a phase in the surgical procedure. A "phase" represents a surgical event that is composed of a series of steps (e.g., closure). A "step" refers to the completion of a named surgical objective (e.g., hemostasis). During each step, certain surgical instruments 108 (e.g., forceps) are used to achieve a specific objective by performing one or more surgical actions.

The video/audio recording system 104 shown in FIG. 1 includes one or more cameras 105, such as operating room cameras, endoscopic cameras, etc. The cameras 105 capture video data of the surgical procedure being performed. The video/audio recording system 104 includes one or more video capture devices that can include cameras 105 placed in the surgical room to capture events surrounding (i.e., outside) the patient being operated upon. The video/audio recording system 104 further includes cameras 105 that are passed inside (e.g., endoscopic cameras) the patient 110 to capture endoscopic data. The endoscopic data provides video and images of the surgical procedure.

The video/audio recording system 104 also includes one or more microphones 107, which can be located on a central console, affixed (e.g., via a clip or other means) to medical personnel or objects in the operating room, and/or attached to or integrated into one or more devices in the operating room. Examples of devices in the operating room can include, but are not limited to surgical tools, video recorders, cameras, goggles, personal computers, smart watches, and/ or smart phones. The microphones 107 capture audio data, and can be wired or wireless or a combination of both.

In exemplary aspects, the video data captured by the cameras 105 and the audio data captured by the microphones 107 both include timestamps (or other indicia) that are used to correlate the video data and the audio data. The timestamps can be used to correlate, or synchronize, the sounds captured in the operating room with the images of the medical procedure performed in the operating room.

The computing system 102 includes one or more memory devices, one or more processors, and a user interface device, among other components. All or a portion of the computing system 102 shown in FIG. 1 can be implemented for example, by all or a portion of computer system 800 of FIG. 8. Computing system 102 can execute one or more computer-executable instructions. The execution of the instructions facilitates the computing system 102 to perform one or more methods, including those described herein. The computing system 102 can communicate with other computing systems via a wired and/or a wireless network. In one or more examples, the computing system 102 includes one or more trained machine learning models that can detect and/or predict features of/from the surgical procedure that is being performed or has been performed earlier. Features can include structures such as anatomical structures, surgical instruments 108 in the captured video of the surgical procedure. Features can further include events such as phases, actions in the surgical procedure. Features that are detected can further include the actor 112 and/or patient 110. Based on the detection, the computing system 102, in one or more examples, can provide recommendations for subsequent actions to be taken by the actor 112. Alternatively, or in addition, the computing system 102 can provide one or more reports based on the detections. The detections by the machine learning models can be performed in an autonomous or semi-autonomous manner.

The machine learning models can include artificial neural networks, such as deep neural networks, convolutional neural networks, recurrent neural networks, encoders, decoders, or any other type of machine learning model. The machine learning models can be trained in a supervised, unsupervised, or hybrid manner. The machine learning models can be trained to perform detection and/or prediction using one or more types of data acquired by the CAS system 100. For example, the machine learning models can use the video data captured via the video/audio recording system 104. Alternatively, or in addition, the machine learning models use the surgical instrumentation data from the surgical instrumentation system 106. In yet other examples, the machine learning models use a combination of video data and surgical instrumentation data.

Additionally, in some examples, the machine learning models can also use audio data captured by the one or microphones 107 during the surgical procedure. The audio data can include sounds emitted by the surgical instrumentation system 106 while activating one or more surgical instruments 108. Alternatively, or in addition, the audio data can include voice commands, snippets, or dialog from one or more actors 112. The audio data can further include sounds made by the surgical instruments 108 during their use.

After training, the one or more machine-learning models can then be used in real-time to process one or more data streams (e.g., video streams, audio streams, RFID data, etc.). The processing can include predicting and characterizing visualization modifications in images of a video of a surgical procedure based on one or more surgical phases, instruments, and/or other structures within various instantaneous or block time periods. The visualization can be modified to highlight the presence, position, and/or use of one or more structures. Alternatively, or in addition, the structures can be used to identify a stage within a workflow (e.g., as represented via a surgical data structure), predict a future stage within a workflow, etc.

In one or more examples, the machine learning models can detect surgical actions, surgical phases, anatomical structures, surgical instruments, activities, events, and various other features from the data associated with a surgical procedure. The detection can be performed in real-time in some examples. Alternatively, or in addition, the computing system 102 analyzes the surgical data, i.e., the various types of data captured during the surgical procedure, in an offline manner (e.g., post-surgery). In one or more examples, the machine learning models detect surgical phases based on detecting some of the features such as the anatomical structure, surgical instruments, etc.

A data collection system 150 can be employed to store the surgical data, including the video(s) captured during the surgical procedures and the audio data captured during the surgical procedure. The data collection system 150 includes one or more storage devices 152. The data collection system 150 can be a local storage system, a cloud-based storage system, or a combination thereof. Further, the data collection system 150 can use any type of cloud-based storage architecture, for example, public cloud, private cloud, hybrid cloud, etc. In some examples, the data collection system can use a distributed storage, i.e., the storage devices 152 are located at different geographic locations. The storage devices 152 can include any type of electronic data storage media used for recording machine-readable data, such as semiconductor-based, magnetic-based, optical-based storage media, or a combination thereof. For example, the data storage media can include flash-based solid-state drives (SSDs), magnetic-based hard disk drives, magnetic tape, optical discs, etc.

In one or more examples, the data collection system 150 can be part of the video/audio recording system 104, or vice-versa. In some examples, the data collection system 150, the video/audio recording system 104, and the computing system 102, can communicate with each other via a communication network, which can be wired, wireless, or a combination thereof. The communication between the systems can include the transfer of data (e.g., video data, audio data, instrumentation data, etc.), data manipulation commands (e.g., browse, copy, paste, move, delete, create, compress, etc.), data manipulation results, etc. In one or more examples, the computing system 102 can manipulate the data already stored/being stored in the data collection system 150 based on outputs from the one or more machine learning models, e.g., phase detection, structure detection, etc. Alternatively, or in addition, the computing system 102 can manipulate the data already stored/being stored in the data collection system 150 based on information from the surgical instrumentation system 106.

In one or more examples, the video captured by the video/audio recording system 104 is stored on the data collection system 150. In some examples, the computing system 102 curates parts of the video data being stored on the data collection system 150. In some examples, the computing system 102 filters the video captured by the video/audio recording system 104 before it is stored on the data collection system 150. Alternatively, or in addition, the computing system 102 filters the video captured by the video/audio recording system 104 after it is stored on the data collection system 150.

In one or more examples, the audio data captured by the video/audio recording system 104 is stored on the data collection system 150. In some examples, the computing system 102 curates parts of the audio data being stored on the data collection system 150. In some examples, the computing system 102 filters (e.g., de-identifies) the audio data captured by the video/audio recording system 104 before it is stored on the data collection system 150. Alternatively, or in addition, the computing system 102 filters the audio data captured by the video/audio recording system 104 after it is stored on the data collection system 150. Audio filtering can include removing specific types of information, types of sounds, or audio channels. For example, background noise, equipment sounds, and/or music can be filtered out through audio filtering in combination with or separately from personal identifying information.

Figure 2:
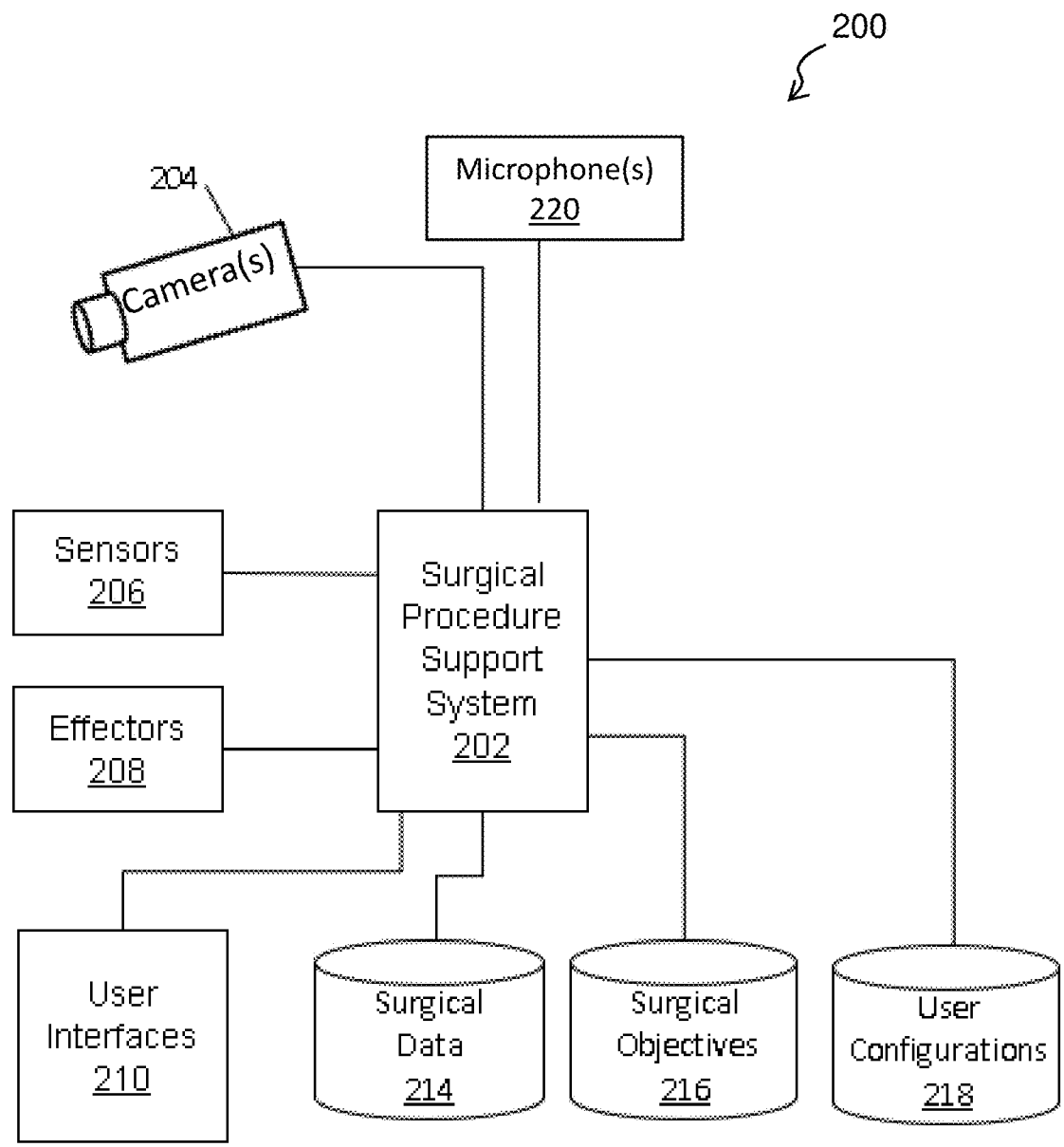
FIG. 2 depicts a surgical procedure system in accordance with one or more aspects.

Turning now to FIG. 2, a surgical procedure system 200 is generally shown in accordance with one or more aspects. The example of FIG. 2 depicts a surgical procedure support system 202 that can include or may be coupled to the CAS system 100 of FIG. 1. The surgical procedure support system 202 can acquire image or video data using one or more cameras 204. The surgical procedure support system 202 can also acquire audio data using one or more microphones 220. The surgical procedure support system 202 can further interface with a plurality of sensors 206 and effectors 208. The sensors 206 may be associated with surgical support equipment and/or patient monitoring. The effectors 208 can be robotic components or other equipment controllable through the surgical procedure support system 202. The surgical procedure support system 202 can also interact with one or more user interfaces 210, such as various input and/or output devices. The surgical procedure support system 202 can store, access, and/or update surgical data 214 associated with a training dataset and/or live data as a surgical procedure is being performed on patient 110 of FIG. 1. The surgical procedure support system 202 can store, access, and/or update surgical objectives 216 to assist in training and guidance for one or more surgical procedures. User configurations 218 can track and store user preferences.

Figure 3:
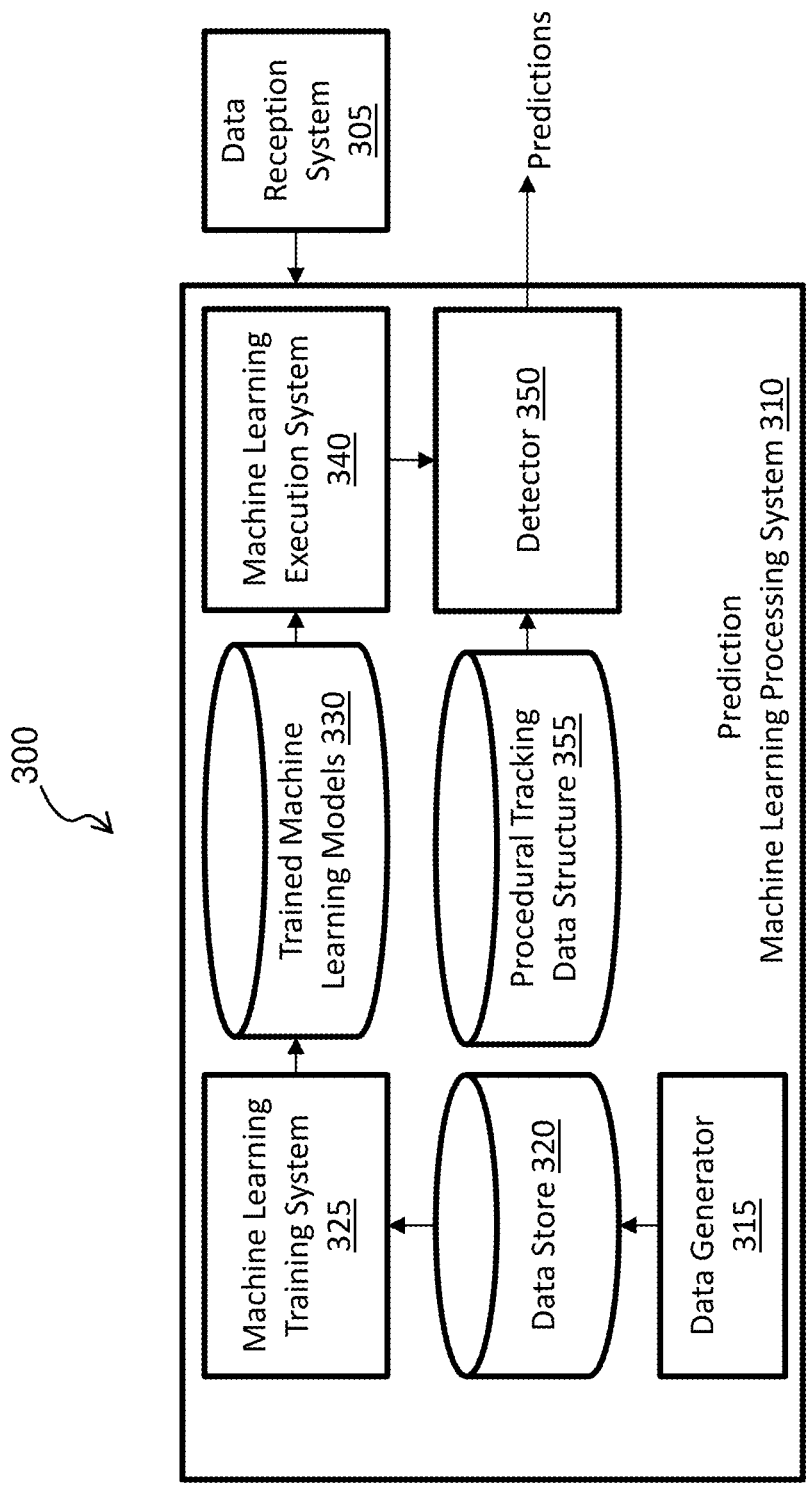
FIG. 3 depicts a system for storing and analyzing audio data and video captured by a video recording system according to one or more aspects.

Turning now to FIG. 3, a system 300 for analyzing data that includes video data is generally shown according to one or more aspects. For example, the video data can be captured from video/audio recording system 104 of FIG. 1. The analysis can result in predicting surgical phases and structures (e.g., instruments, anatomical structures, etc.) in the video data using machine learning. System 300 can be the CAS system 100 of FIG. 1, or a part thereof in one or more examples. System 300 uses data streams in the surgical data to identify procedural states according to some aspects.

System 300 includes a data reception system 305 that collects surgical data, including the video data and surgical instrumentation data. The data reception system 305 can include one or more devices (e.g., one or more user devices and/or servers) located within and/or associated with a surgical operating room and/or control center. The data reception system 305 can receive surgical data in real-time, i.e., as the surgical procedure is being performed. Alternatively, or in addition, the data reception system 305 can receive or access surgical data in an offline manner, for example, by accessing data that is stored in the data collection system 150 of FIG. 1.

System 300 further includes a machine learning processing system 310 that processes the surgical data using one or more machine learning models to identify one or more features, such as surgical phase, instrument, anatomical structure, etc., in the surgical data. It will be appreciated that machine learning processing system 310 can include one or more devices (e.g., one or more servers), each of which can be configured to include part or all of one or more of the depicted components of the machine learning processing system 310. In some instances, a part or all of the machine learning processing system 310 is in the cloud and/or remote from an operating room and/or physical location corresponding to a part or all of data reception system 305. It will be appreciated that several components of the machine learning processing system 310 are depicted and described herein. However, the components are just one example structure of the machine learning processing system 310, and that in other examples, the machine learning processing system 310 can be structured using a different combination of the components. Such variations in the combination of the components are encompassed by the technical solutions described herein.

The machine learning processing system 310 includes a machine learning training system 325, which can be a separate device (e.g., server) that stores its output as one or more trained machine learning models 330. The machine learning models 330 are accessible by a machine learning execution system 340. The machine learning execution system 340 can be separate from the machine learning training system 325 in some examples. In other words, in some aspects, devices that "train" the models are separate from devices that "infer," i.e., perform real-time processing of surgical data using the trained machine learning models 330.

Machine learning processing system 310, in some examples, further includes a data generator 315 to generate simulated surgical data, such as a set of virtual images, or record the video data from the video/audio recording system 104, to train the machine learning models 330. Data generator 315 can access (read/write) a data store 320 to record data, including multiple images and/or multiple videos. The images and/or videos can include images and/or videos collected during one or more procedures (e.g., one or more surgical procedures). For example, the images and/or video may have been collected by a user device worn by the actor 112 of FIG. 1 (e.g., surgeon, surgical nurse, anesthesiologist, etc.) during the surgery, a non-wearable imaging device located within an operating room, or an endoscopic camera inserted inside the patient 110 of FIG. 1. The data store 320 is separate from the data collection system 150 of FIG. 1 in some examples. In other examples, the data store 320 is part of the data collection system 150.

Each of the images and/or videos recorded in the data store 320 for training the machine learning models 330 can be defined as a base image and can be associated with other data that characterizes an associated procedure and/or rendering specifications. For example, the other data can identify a type of procedure, a location of a procedure, one or more people involved in performing the procedure, surgical objectives, and/or an outcome of the procedure. Alternatively, or in addition, the other data can indicate a stage of the procedure with which the image or video corresponds, rendering specification with which the image or video corresponds and/or a type of imaging device that captured the image or video (e.g., and/or, if the device is a wearable device, a role of a particular person wearing the device, etc.). Further, the other data can include image-segmentation data that identifies and/or characterizes one or more objects (e.g., tools, anatomical objects, etc.) that are depicted in the image or video. The characterization can indicate the position, orientation, or pose of the object in the image. For example, the characterization can indicate a set of pixels that correspond to the object and/or a state of the object resulting from a past or current user handling. Localization can be performed using a variety of techniques for identifying objects in one or more coordinate systems.

The machine learning training system 325 uses the recorded data in the data store 320, which can include the simulated surgical data (e.g., set of virtual images) and actual surgical data to train the machine learning models 330. The machine learning model 330 can be defined based on a type of model and a set of hyperparameters (e.g., defined based on input from a client device). The machine learning models 330 can be configured based on a set of parameters that can be dynamically defined based on (e.g., continuous or repeated) training (i.e., learning, parameter tuning). Machine learning training system 325 can use one or more optimization algorithms to define the set of parameters to minimize or maximize one or more loss functions. The set of (learned) parameters can be stored as part of a trained machine learning model 330 using a specific data structure for that trained machine learning model 330. The data structure can also include one or more non-learnable variables (e.g., hyperparameters and/or model definitions).

Machine learning execution system 340 can access the data structure(s) of the machine learning models 330 and accordingly configure the machine learning models 330 for inference (i.e., prediction). The machine learning models 330 can include, for example, a fully convolutional network adaptation, an adversarial network model, an encoder, a decoder, or other types of machine learning models. The type of the machine learning models 330 can be indicated in the corresponding data structures. The machine learning model 330 can be configured in accordance with one or more hyperparameters and the set of learned parameters.

The one or more machine learning models 330, during execution, receive, as input, surgical data to be processed and subsequently generate one or more inferences according to the training. For example, the video data captured by the video/audio recording system 104 of FIG. 1 can include data streams (e.g., an array of intensity, depth, and/or RGB values) for a single image or for each of a set of frames (e.g., including multiple images or an image with sequencing data) representing a temporal window of fixed or variable length in a video. The video data that is captured by the video/audio recording system 104 can be received by the data reception system 305, which can include one or more devices located within an operating room where the surgical procedure is being performed. Alternatively, the data reception system 305 can include devices that are located remotely, to which the captured video data is streamed live during the performance of the surgical procedure. Alternatively, or in addition, the data reception system 305 accesses the data in an offline manner from the data collection system 150 or from any other data source (e.g., local or remote storage device).

The data reception system 305 can process the video and/or other data received. The processing can include decoding when a video stream is received in an encoded format such that data for a sequence of images can be extracted and processed. The data reception system 305 can also process other types of data included in the input surgical data. For example, the surgical data can include additional data streams, such as audio data, RFID data, textual data, measurements from one or more surgical instruments/sensors, etc., that can represent stimuli/procedural states from the operating room. The data reception system 305 synchronizes the different inputs from the different devices/sensors before inputting them in the machine learning processing system 310. In according to some aspects, the audio data is de-identified as described below with reference to FIGS. 4-7 prior to being synchronized by the data reception system 305 and input to machine learning processing system 310. Synchronization can be achieved by using a common reference clock to generate time stamps alongside each data stream. The clocks can be shared via network protocols or through hardware locking or through any other means. Such time stamps can be associated with any processed data format, such as, but not limited to text or other discrete data created from the audio signal. Additional synchronization can be performed by linking actions, events, or phase segmented that have been automatically processed from the raw signals using machine learning models. For example, text generated from an audio signal can be associated to specific phases of the procedure that are extracted from that audio or any other data stream signal. De-identified text or any other processed form of data can then also be processed to generate new audio and associated with the relevant part of the original signal.

The machine learning models 330, once trained, can analyze the input surgical data, and in one or more aspects, predict and/or characterize structures included in the video data included with the surgical data. The video data can include sequential images and/or encoded video data (e.g., using digital video file/stream formats and/or codecs, such as MP4, MOV, AVI, WEBM, AVCHD, OGG, etc.). The prediction and/or characterization of the structures can include segmenting the video data or predicting the localization of the structures with a probabilistic heatmap. In some instances, the one or more machine learning models include or are associated with a preprocessing or augmentation (e.g., intensity normalization, resizing, cropping, etc.) that is performed prior to segmenting the video data. An output of the one or more machine learning models can include image-segmentation or probabilistic heatmap data that indicates which (if any) of a defined set of structures are predicted within the video data, a location and/or position and/or pose of the structure(s) within the video data, and/or state of the structure(s). The location can be a set of coordinates in an image/frame in the video data. For example, the coordinates can provide a bounding box. The coordinates can provide boundaries that surround the structure(s) being predicted. The trained machine learning models 330, in one or more examples, are trained to perform higher-level predictions and tracking, such as predicting a phase of a surgical procedure and tracking one or more surgical instruments used in the surgical procedure.

While some techniques for predicting a surgical phase ("phase") in the surgical procedure are described herein, it should be understood that any other technique for phase prediction can be used without affecting the aspects of the technical solutions described herein. In some examples, the machine learning processing system 310 includes a detector 350 that uses the machine learning models to identify a phase within the surgical procedure ("procedure"). Detector 350 uses a particular procedural tracking data structure 355 from a list of procedural tracking data structures. Detector 350 selects the procedural tracking data structure 355 based on the type of surgical procedure that is being performed. In one or more examples, the type of surgical procedure is predetermined or input by actor 112. The procedural tracking data structure 355 identifies a set of potential phases that can correspond to a part of the specific type of procedure.

In some examples, the procedural tracking data structure 355 can be a graph that includes a set of nodes and a set of edges, with each node corresponding to a potential phase. The edges can provide directional connections between nodes that indicate (via the direction) an expected order during which the phases will be encountered throughout an iteration of the procedure. The procedural tracking data structure 355 may include one or more branching nodes that feed to multiple next nodes and/or can include one or more points of divergence and/or convergence between the nodes. In some instances, a phase indicates a procedural action (e.g., surgical action) that is being performed or has been performed and/or indicates a combination of actions that have been performed. In some instances, a phase relates to a biological state of a patient undergoing a surgical procedure. For example, the biological state can indicate a complication (e.g., blood clots, clogged arteries/veins, etc.), pre-condition (e.g., lesions, polyps, etc.). In some examples, the machine learning models 330 are trained to detect an "abnormal condition," such as hemorrhaging, arrhythmias, blood vessel abnormality, etc.

Each node within the procedural tracking data structure 355 can identify one or more characteristics of the phase corresponding to that node. The characteristics can include visual characteristics. In some instances, the node identifies one or more tools that are typically in use or availed for use (e.g., on a tool tray) during the phase. The node also identifies one or more roles of people who are typically performing a surgical task, a typical type of movement (e.g., of a hand or tool), etc. Thus, detector 350 can use the segmented data generated by machine learning execution system 340 that indicates the presence and/or characteristics of particular objects within a field of view to identify an estimated node to which the real image data corresponds. Identification of the node (i.e., phase) can further be based upon previously detected phases for a given procedural iteration and/or other detected input (e.g., verbal audio data that includes person-to-person requests or comments, explicit identifications of a current or past phase, information requests, etc.).

The detector 350 outputs the prediction associated with a portion of the video data that is analyzed by the machine learning processing system 310. The prediction is associated with the portion of the video data by identifying a start time and an end time of the portion of the video that is analyzed by the machine learning execution system 340. The prediction that is output can include an identity of a surgical phase, activity, or event as detected by the detector 350 based on the output of the machine learning execution system 340. Further, the prediction, in one or more examples, can include identities of the structures (e.g., instrument, anatomy, etc.) that are identified by the machine learning execution system 340 in the portion of the video that is analyzed. The prediction can also include a confidence score of the prediction. Various types of information in the prediction that can be output may include phases, actions, and/or events associated with a surgical procedure.

It should be noted that although some of the drawings depict endoscopic videos being analyzed, the technical solutions described herein can be applied to analyze video and image data captured by cameras that are not endoscopic (i.e., cameras external to the patient's body) when performing open surgeries (i.e., not laparoscopic surgeries). For example, the video and image data can be captured by cameras that are mounted on one or more personnel in the operating room, e.g., surgeon. Alternatively, or in addition, the cameras can be mounted on surgical instruments, walls, or other locations in the operating room.

Figure 4:
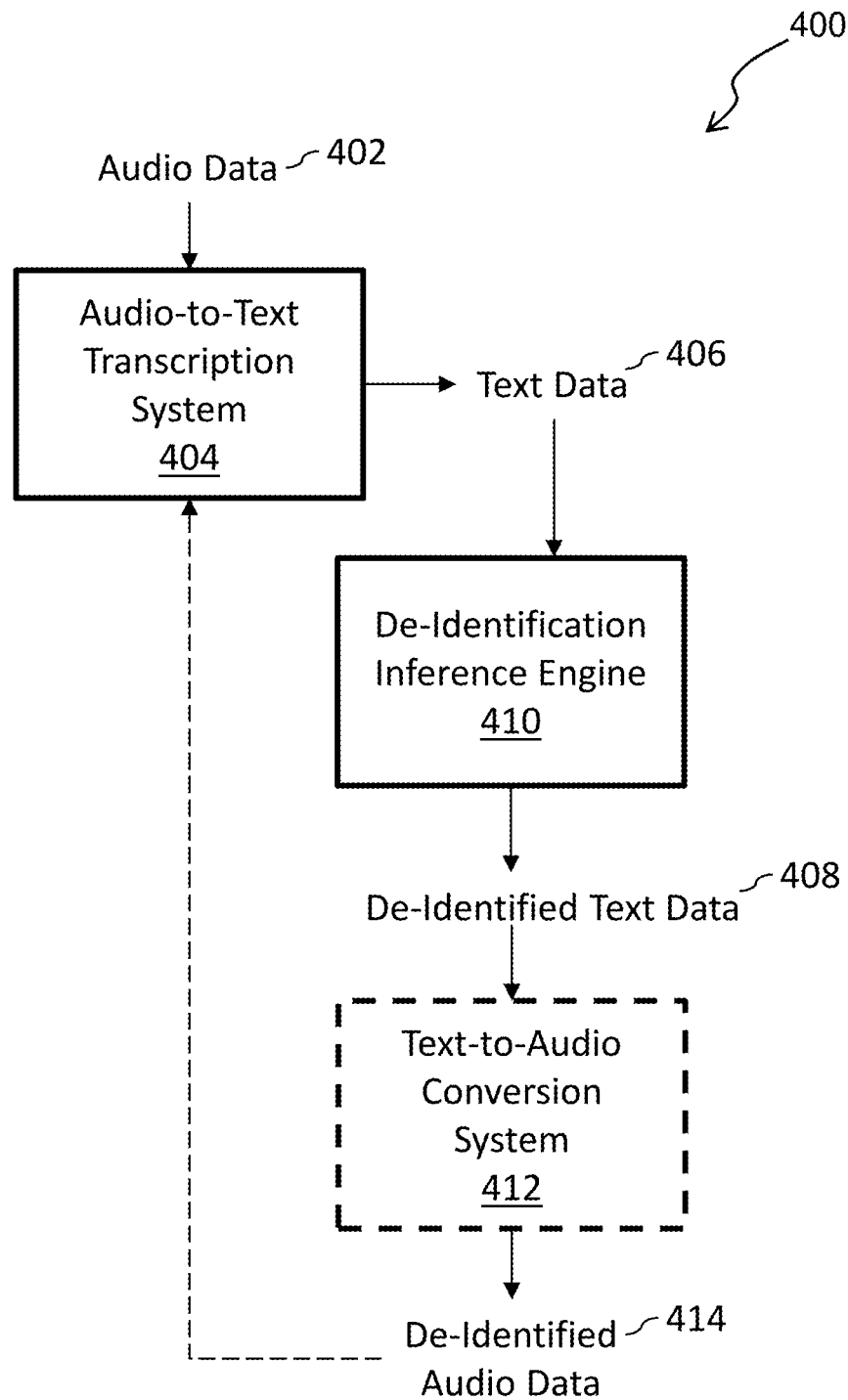
FIG. 4 depicts a block diagram of a system for de-identifying data obtained from microphones according to one or more aspects.

Turning now to FIG. 4, a block diagram of components of a system 400 for de-identifying data obtained from a microphone is generally shown in accordance with one or more aspects. All or a portion of the system 400 can be implemented by CAS system 100 of FIG. 1, and/or by computer system 800 of FIG. 8. In addition, all or a portion of the processing described in reference to FIG. 4 can be performed by data reception system 305 of FIG. 3 and/or data generator 315 of FIG. 3.

As shown in FIG. 4, audio data 402 is input to an audio-to-text transcription system 404 to generate text data. The audio data 402 is received from one or microphones such as microphone 107 of FIG. 1 and/or microphone 220 of FIG. 2. The audio data 402 can be digital audio data that is stored in an audio file format. As known in the art, the bit layout of the audio data (excluding metadata) is referred to as the audio coding format. The audio coding format can be an uncompressed format such as, but not limited to: LPCM, WAV, AIFF, and/or AU. To save on storage space, a compressed format can be used such as, but not limited to: FLAC, WavPack, ALAC, MPEG, Opus, and/or MP3. In some aspects the microphone 107 of FIG. 1 and/or microphone 220 of FIG. 2 can be wearable microphones, component-integrated microphones, directional microphones, and/or other types of microphones known in the art.

The audio data 402 is input to an audio-to-text transcription system 404 which can be implemented by any audio-to-text transcription application known in the art such as, but not limited to: Record and Transcribe from Temi, Go Transcribe from Go-Transcribe Ltd., and/or Call Recorder from Rev. In according to one or more aspects, the audio-to-text transcription system 404 outputs discrete data, such as text data 406. for input to de-identification inference engine 410. The format of the text data 406 may be any text format known in the art such as, but not limited to plain text format, doc format, and/or rich text file format. De-identification inference engine 410 is an example of a machine learning execution system. Aspects of the invention described herein use text data as an example of discrete data that the continuous stream of audio data can be converted into for input to an inference engine for de-identification. Aspects of the invention are not limited to text data in a text data format, as discrete data in other formats that are generated based on the audio data can also be implemented by one or more aspects of the invention.

As shown in FIG. 4, the text data 406 is input to a de-identification inference engine 410 to generate de-identified text data 408 that is a copy of the text data 406 with portions of the text data 406 that could be used to identify a particular person or other entity removed or replaced. For example, the text data 406 may include a phrase that often used by a particular medical provider, a phrase that is typically used by people in particular geographic locations, or a name of a medical provider or patient. The de-identified text data 408 would have these identifying references removed or replaced with non-identifying references. For example, the text data 406 "Sally hand me the gauze" could be converted to the de-identified text data 408 "hand me the gauze." A phrase such as "y'all" which is typically used in southern states in the United States could be converted to "you all" or "you" or some other phrase or removed entirely depending on the context. A medical provider may be known to be a sports fan of a particular team or to have a particular hobby and references to particular sports teams or activities can be removed or obscured from the text data.

The training and operation of the de-identification inference engine 410 are described further below in reference to FIG. 5 and FIG. 6. In according to aspects of the invention, the de-identified text data 408 is synchronized with the video data or other data captured by the video/audio recording system 104.

In according to other aspects, the de-identified text data 408 is converted back into audio data prior to being synchronized with the other data. As shown in FIG. 4, this is performed by a text-to-audio conversion system 412 which generates de-identified audio data 414 based on the de-identified text data 408. The text-to-audio conversion system 412 can be implemented by any text-to-audio conversion application known in the art such as, but not limited to: Dragon from Nuance; Polly from Amazon; and/or Voice Reader from Linguatec. In some aspects, the audio-to-text transcription system 404 can be combined with the text-to-audio conversion system 412. Further, the de-identified audio data 414 can be fed back to the audio-to-text transcription system 404 to output text data 406 with the de-identified information removed for use by other text-based systems.

All or a portion of the components of the system 400 shown in FIG. 4 can be integrated into the system 300 shown in FIG. 3. For example, according to one more aspects of the invention, the audio-to-text transcription system 404 and the de-identification inference engine 410 are integrated into the data reception system 305 of the system 300 shown in FIG. 3.

All or portion of the audio data 402, text data 406, de-identified text data 408, and de-identified audio data 414 can be stored in storage device 152 of FIG. 1, surgical data 214 of FIG. 2, and/or in another storage device.

In according to aspects, the audio does not need to be converted into text for de-identification. Any high-level abstraction can be used, for example specific audio signal recognition systems can be used instead to augment the signal. Text is just one form of a meta-label or structured representation of a continuous signal. In according to aspects, a label (in a discrete format) can be used along with or instead of the text. Example of labels include, but are not limited to name, phase, event, etc.

Different audio data receivers can be treated as independent or have specific prior information associated to them in order to help a machine learning system that is processing data received at that node to be more efficient. Prior information could be, but is not limited to, information about the individuals near the receiver, the receivers' location, etc. Additionally, the relative placement of microphones may be known (e.g., to the system and/or to other microphones) and use this information to support processing.

The computing environment of FIG. 4 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various aspects.

It is to be understood that the block diagram of FIG. 4 is not intended to indicate that system 400 is to include all of the components shown in FIG. 4. Rather, the system 400 can include any appropriate fewer or additional components not illustrated in FIG. 4, such as but not limited to removal of the text-to-audio conversion system 412. In addition, the components shown in FIG. 4 may be arranged differently. For example, the audio-to-text transcription system 404 and the text-to-audio conversion system 412 may be provided by the same application.

Figure 5:
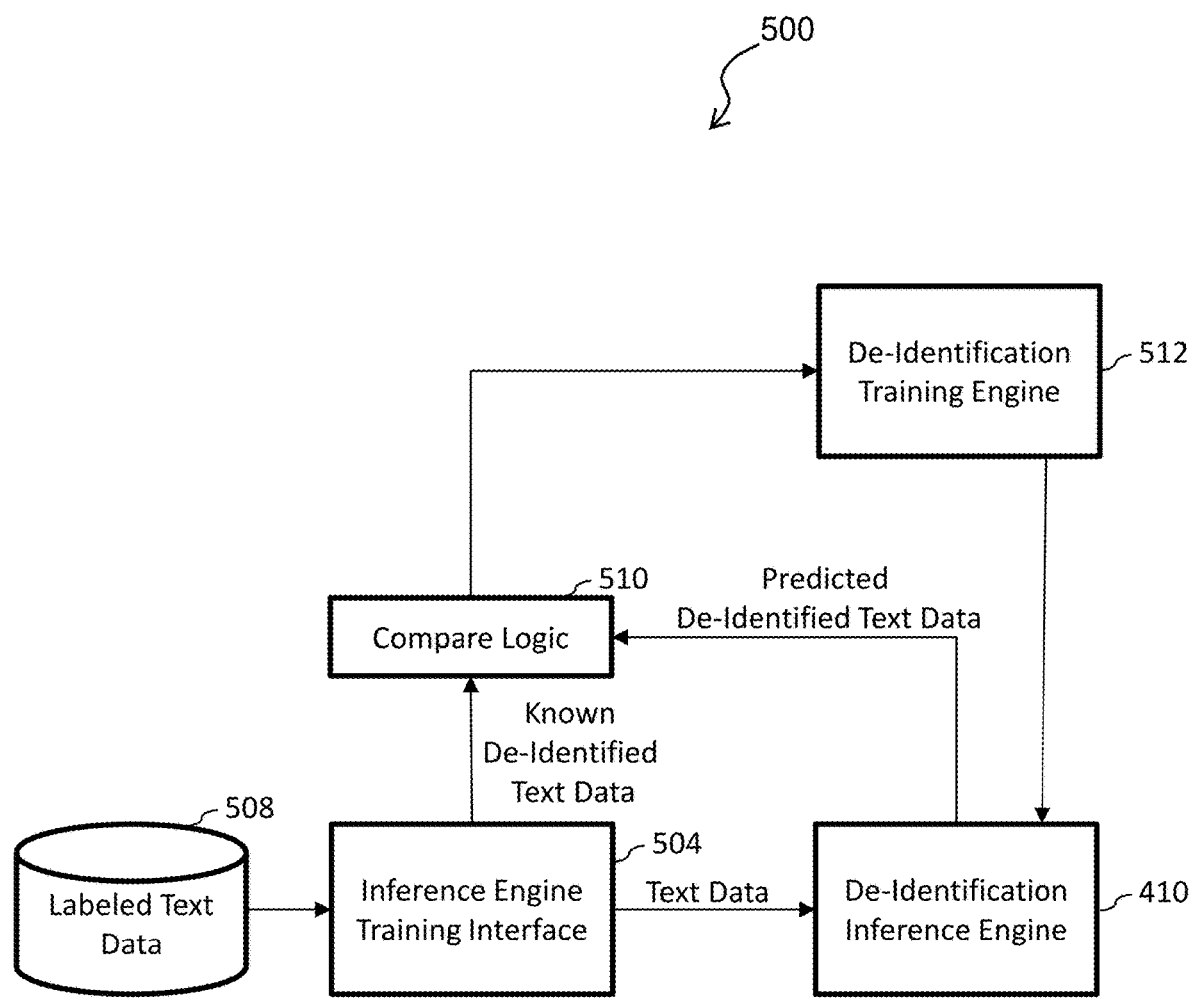
FIG. 5 depicts a block diagram of a system for training a neural network inference engine to de-identify data obtained from microphones according to one or more aspects.

Turning FIG. 5, a block diagram of components of a system 500 for training the de-identification inference engine 410 to de-identify data obtained from microphones is generally shown in accordance with one or more aspects. All or a portion of the system 500 can be implemented by CAS system 100 of FIG. 1, and/or by computer system 800 of FIG. 8. In addition, all or a portion of the processing described in reference to FIG. 4 can be performed using data generator 315, data store 320, machine learning training system 325, trained machine learning models 330, and/or machine learning execution system 340 of FIG. 3.

As shown in FIG. 5, a database of labeled text data 508 is input to an inference engine training interface 504. The labeled text data 508 includes text data such as text data 406 of FIG. 4 and its corresponding de-identified text data such as de-identified text data 408 of FIG. 4. In according to aspects, the de-identified text data 408 for a corresponding text data 406 is provided by or verified by a human analyst. For example, the labeled text data 508 may include a list of keywords or multi word phrases having the potential to identify an entity (i.e., the text data) and corresponding text data (i.e., the de-identified text) with the keywords or phrases removed or replaced. The labeled text data 508 does not have to correlate to a specific list of keywords or phrases, and it may include a term or phrase that includes a proper name or date, and the training includes identifying any proper names or date (and not just names/dates specified in a list). As used herein, the term "phrase" refers to one or more words in either a text format or an audio format. Where a phrase includes multiple words, the phrase may be parsed into groups of one or more words deemed to be related, e.g., subphrases. The labeled text data 508 can include sets of phrases, with each set including a phrase and its corresponding de-identified phrase. The phrases and its corresponding de-identified phrase are the same when the phrase does not include any patterns, or words, that are likely to identify a specific entity.

In accordance with aspects of the present invention, the machine learning systems can use a classifier trained to compute a likelihood score for phrases, and results with a score above a threshold value can be designated as likely to identify a specific entity. In addition, temporal windows can be applied to consecutive predictions of the likelihood to handle prediction noise.

As shown in FIG. 5, the inference engine training interface 504 splits each set of phrases in the labeled text data 508 into text data (shown in FIG. 5 as "text data") and its corresponding label (shown in FIG. 5 as "known de-identified text data"). In some aspects, the text data is input to the de-identification inference engine 410 by the inference engine training interface 504 in batches of sets of phrases and labels (shown in FIG. 5 as "predicted de-identified text data") are predicted for each set in the batch. In addition, the inference engine training interface 504 sends the known, ground truth label (shown in FIG. 5 as "known de-identified text data") of each set to compare logic 510.

As shown in FIG. 5, the predicted de-identified text data is compared to the known de-identified text data by the compare logic 510. In some aspects of the present invention, the compare logic 510 uses a loss function to compare the predicted label with the ground truth label. When the de-identification inference engine 410 includes a neural network, the results of the comparison are input to de-identification training engine 512 to determine adjustments to neural network biases and weightings to improve accuracy and reduce the loss function. The determined adjustments are input to the de-identification inference engine 410. The process shown in FIG. 5 is repeated iteratively to minimize the loss function and maximize the accuracy of predictions. In one or more embodiments of the present invention, portions of the neural network shown in FIG. 5 are implemented by off-the-shelf software. For example, the Google Tensorflow open-source Python library of mathematical routines can be used to implement the neural network.

In one or more aspects of the present invention, the de-identification inference engine 410 generates de-identified text data based solely on a list of specific keywords and specific de-identifying actions (e.g., remove, or replace with word "x"). In one or more other aspects of the present invention, the de-identification inference engine 410 combines the use of a list of specific keywords and actions with a neural network to determine other keywords and phrases (e.g., proper nouns) to be de-identified and an action to take to perform the de-identification. These two approaches combined allow for specific known identifiers to be removed along with more general categories of identifiers (proper nouns, general discussion about sports or hobbies, etc.).

De-identification will transform phrases to be neutral. A few non-limiting examples follow. In a first example, the phrase "Maria can you place retractor in port" can be transformed into "Support staff place retractor in port." In a second example, the phrases "Were scans from X Hospital sent? Do you have files on patient Y, who will be operated next?" can be transformed into "Were scans sent for next patient?"

Once the de-identification inference engine 410 is trained to a desired level of accuracy and has been tested against previously unseen data, the training components are removed and the de-identification inference engine 410 can be used to de-identify data received from microphones.

There are a variety of times when retraining of the de-identification inference engine 410 can be useful, for example, when new medical provider personnel are expected to perform or assist with performing surgeries, and when new equipment is utilized in an operating room.

In accordance with one or more aspects of the technical solutions described herein, de-identification inference engine 410 output is validated on a periodic bases by comparing it with human output (e.g., labels). When incorrect results are found, these are added to the network training process by being randomly assigned either to a training set or to a validation set. In this way the training data increases and leads to a more accurate inference engine. In addition, adding to the validation set can result in a more statistically significant measure of the accuracy of the inference engine. The auditing process can be automated so that the inference engines continually improve their learning.

The computing environment of FIG. 5 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various aspects.

It is to be understood that the block diagram of FIG. 5 is not intended to indicate that system 500 is to include all of the components shown in FIG. 5. Rather, the system 500 can include any appropriate fewer or additional components not illustrated in FIG. 5. In addition, the components shown in FIG. 5 may be arranged differently.

Figure 6:
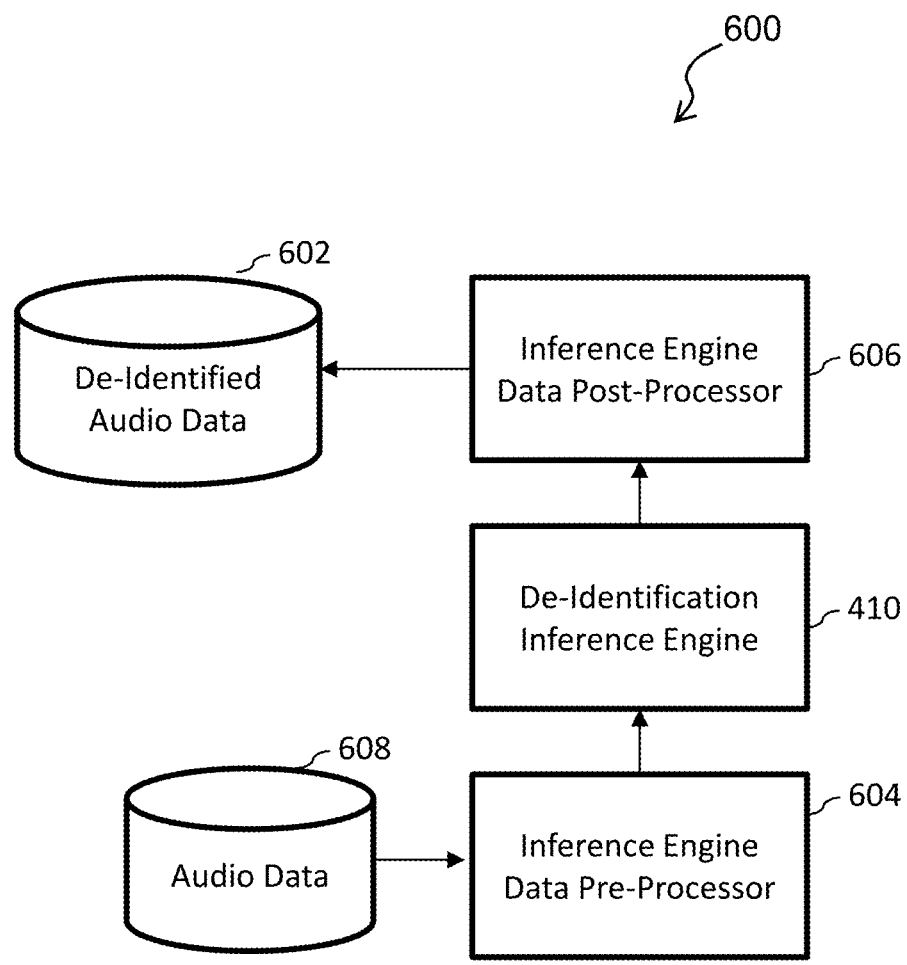
FIG. 6 depicts a block diagram of a system for using a neural network inference engine to de-identify data obtained from microphones according to one or more aspects.

Turning now to FIG. 6, a block diagram of components of a system 600 for using an inference engine to de-identify data obtained from microphones is generally shown in accordance with one or more aspects. All or a portion of the system 600 can be implemented by CAS system 100 of FIG. 1, and/or by computer system 800 of FIG. 8. In addition, all or a portion of the processing described in reference to FIG. 6 can be performed using data reception system 305 and/or machine learning execution system 340 of FIG. 3.

As shown in FIG. 6, audio data 608, such as audio data 402 of FIG. 4, is obtained from one or more microphones is input to inference engine data pre-processor 604. In the example shown in FIG. 6, the de-identification inference engine 410 operates on data in a text format, and the inference engine data pre-processor 604 converts the audio data 608 into a text format. This can be performed, for example by the audio-to-text transcription system 404 of FIG. 4. De-identified text data, such as de-identified text data 408 of FIG. 4, is output by the de-identification inference engine 410 to inference engine data post-processor 606. As shown in FIG. 6, the inference engine data post-processor 606 converts the de-identified text data into de-identified audio data 602. This conversion can be performed for example, by text-to-audio conversion system 412 of FIG. 4.

According to one or more aspects the audio data also includes one or more timestamps that are maintained throughout the processing shown in FIG. 6. The timestamps can be used to correlate the de-identified audio data to other data collected (e.g., by a camera or video device) during the surgery.

The computing environment of FIG. 6 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various aspects.

It is to be understood that the block diagram of FIG. 6 is not intended to indicate that system 600 is to include all of the components shown in FIG. 6. Rather, the system 600 can include any appropriate fewer or additional components not illustrated in FIG. 6. For example, de-identified text data may be used by the next step which would eliminate the need for the inference engine data post-processor 606. In addition, the components shown in FIG. 6 may be arranged differently.

Figure 7:
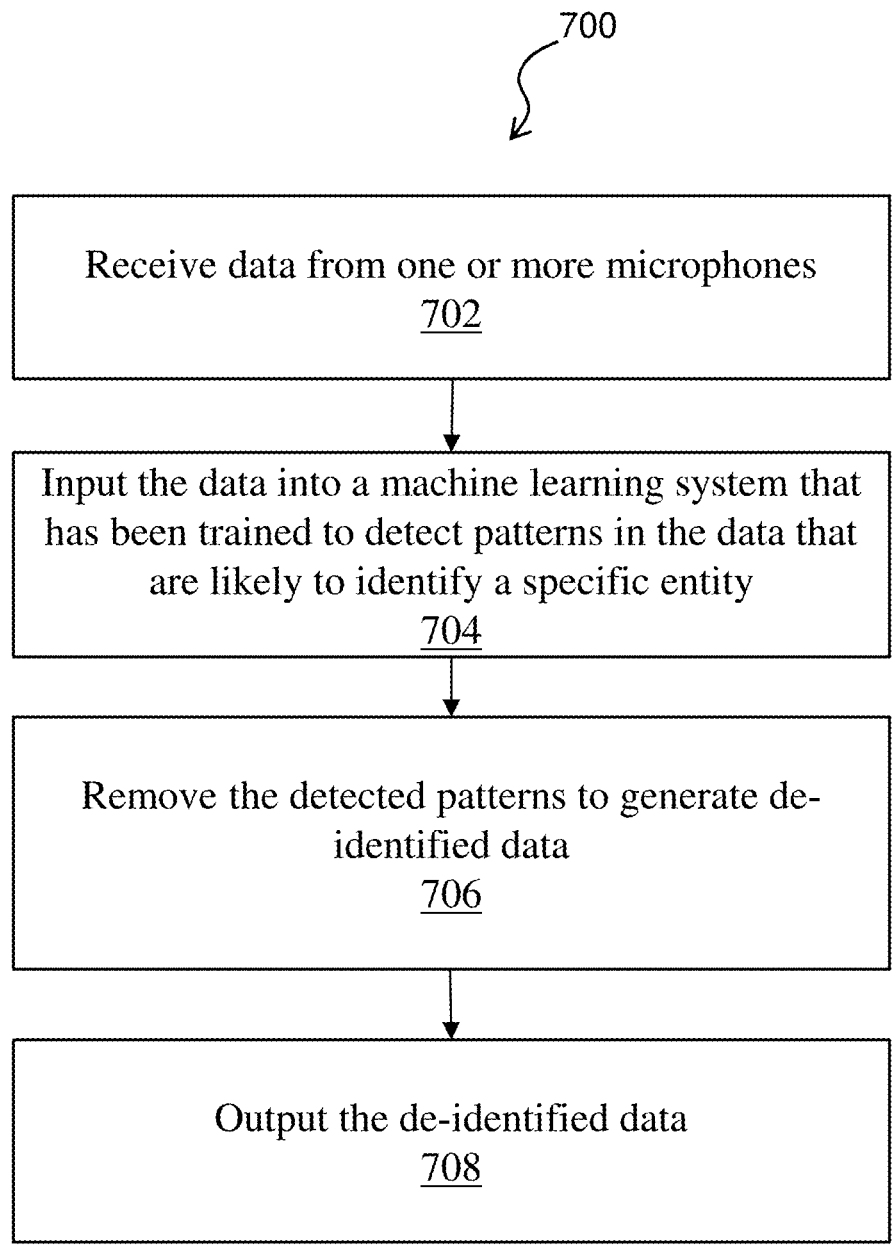
FIG. 7 depicts a flowchart of a method for de-identifying data obtained from microphones according to one or more aspects.

Turning now to FIG. 7, a flowchart of a method 700 for de-identifying data obtained from microphones is generally shown in accordance with one or more aspects. All or a portion of method 700 can be implemented, for example, by all or a portion of CAS system 100 of FIG. 1 and/or computer system 800 of FIG. 8. At block 702, data is received from one or more microphones. According to some aspects, when the data that is received is in an audio format, the data can be converted into a text format before being input to the machine learning system. The conversion is performed when the machine learning system is trained to operate on data in a text format.

At blocks 704 and 706, the data is de-identified. The data is input, at block 704, to a machine learning system that has been trained to detect patterns in the data that are likely to identify a specific entity. At block 706, the de-identified data is generated by removing the detected patterns. The removing can include eliminating a phrase completely or replacing the patterns (e.g., phrases) with another phrase. As used herein, a phrase is a type of pattern that can include one or more words.

At block 708, the de-identified data is output. The de-identified data can be in a text format or it can be converted into an audio format. As described previously, the de-identified data can be synchronized with other data captured during the same time period and used for training or other purposes where it is important to preserve patient or medical provider anonymity. The de-identified data can also be input to another machine learning system, such machine learning processing system 310 of FIG. 3.

The processing shown in FIG. 7 is not intended to indicate that the operations are to be executed in any particular order or that all of the operations shown in FIG. 7 are to be included in every case. Additionally, the processing shown in FIG. 7 can include any suitable number of additional operations.

Figure 8:
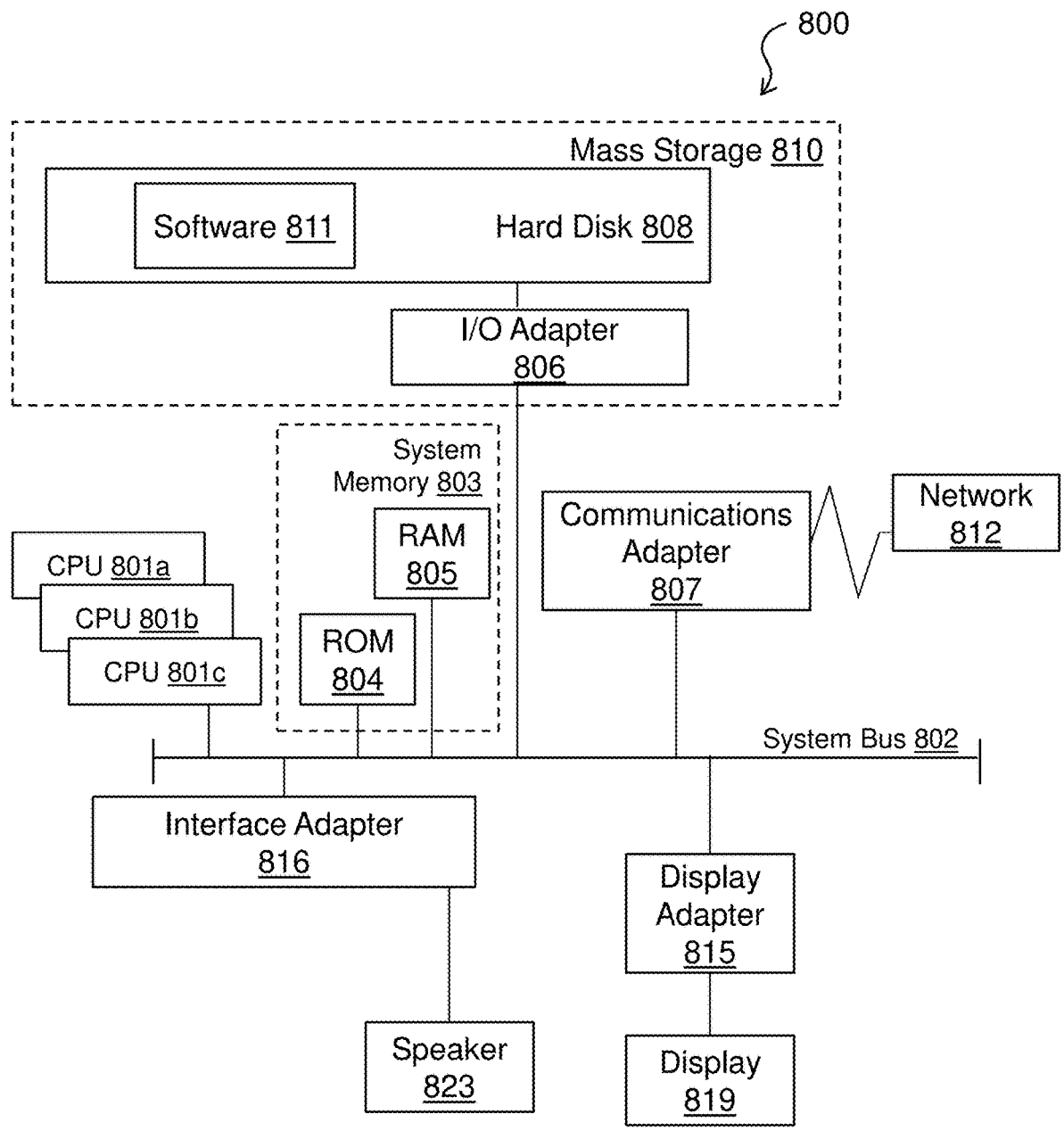
FIG. 8 depicts a computer system according to one or more aspects.

Turning now to FIG. 8, a computer system 800 is generally shown in accordance with an aspect. The computer system 800 can be an electronic computer framework comprising and/or employing any number and combination of computing devices and networks utilizing various communication technologies, as described herein. The computer system 800 can be easily scalable, extensible, and modular, with the ability to change to different services or reconfigure some features independently of others. The computer system 800 may be, for example, a server, desktop computer, laptop computer, tablet computer, or smartphone. In some examples, computer system 800 may be a cloud computing node. Computer system 800 may be described in the general context of computer-executable instructions, such as program modules, being executed by a computer system. Generally, program modules may include routines, programs, objects, components, logic, data structures, and so on that perform particular tasks or implement particular abstract data types. Computer system 800 may be practiced in distributed cloud computing environments where tasks are performed by remote processing devices that are linked through a communications network. In a distributed cloud computing environment, program modules may be located in both local and remote computer system storage media, including memory storage devices.

As shown in FIG. 8, the computer system 800 has one or more central processing units (CPU(s)) 801*a*, 801*b*, 801*c*, etc. (collectively or generically referred to as processor(s) 801). The processors 801 can be a single-core processor, multi-core processor, computing cluster, or any number of other configurations. The processors 801 can be any type of circuitry capable of executing instructions. The processors 801, also referred to as processing circuits, are coupled via a system bus 802 to a system memory 803 and various other components. The system memory 803 can include one or more memory devices, such as read-only memory (ROM) 804 and a random-access memory (RAM) 805. The ROM 804 is coupled to the system bus 802 and may include a basic input/output system (BIOS), which controls certain basic functions of the computer system 800. The RAM is read-write memory coupled to the system bus 802 for use by the processors 801. The system memory 803 provides temporary memory space for operations of said instructions during operation. The system memory 803 can include random access memory (RAM), read-only memory, flash memory, or any other suitable memory systems.

The computer system 800 comprises an input/output (I/O) adapter 806 and a communications adapter 807 coupled to the system bus 802. The I/O adapter 806 may be a small computer system interface (SCSI) adapter that communicates with a hard disk 808 and/or any other similar component. The I/O adapter 806 and the hard disk 808 are collectively referred to herein as a mass storage 810.

Software 811 for execution on the computer system 800 may be stored in the mass storage 810. The mass storage 810 is an example of a tangible storage medium readable by the processors 801, where the software 811 is stored as instructions for execution by the processors 801 to cause the computer system 800 to operate, such as is described hereinbelow with respect to the various Figures. Examples of computer program product and the execution of such instruction is discussed herein in more detail. The communications adapter 807 interconnects the system bus 802 with a network 812, which may be an outside network, enabling the computer system 800 to communicate with other such systems. In one aspect, a portion of the system memory 803 and the mass storage 810 collectively store an operating system, which may be any appropriate operating system to coordinate the functions of the various components shown in FIG. 8.

Additional input/output devices are shown as connected to the system bus 802 via a display adapter 815 and an interface adapter 816 and. In one aspect, the adapters 806, 807, 815, and 816 may be connected to one or more I/O buses that are connected to the system bus 802 via an intermediate bus bridge (not shown). A display 819 (e.g., a screen or a display monitor) is connected to the system bus 802 by a display adapter 815, which may include a graphics controller to improve the performance of graphics-intensive applications and a video controller. A keyboard, a mouse, a touchscreen, one or more buttons, a speaker, etc., can be interconnected to the system bus 802 via the interface adapter 816, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 8, the computer system 800 includes processing capability in the form of the processors 801, and storage capability including the system memory 803 and the mass storage 810, input means such as the buttons, touchscreen, and output capability including the speaker 823 and the display 819.

In some aspects, the communications adapter 807 can transmit data using any suitable interface or protocol, such as the internet small computer system interface, among others. The network 812 may be a cellular network, a radio network, a wide area network (WAN), a local area network (LAN), or the Internet, among others. An external computing device may connect to the computer system 800 through the network 812. In some examples, an external computing device may be an external web server or a cloud computing node.

It is to be understood that the block diagram of FIG. 8 is not intended to indicate that the computer system 800 is to include all of the components shown in FIG. 8. Rather, the computer system 800 can include any appropriate fewer or additional components not illustrated in FIG. 8 (e.g., additional memory components, embedded controllers, modules, additional network interfaces, etc.). Further, the aspects described herein with respect to computer system 800 may be implemented with any appropriate logic, wherein the logic, as referred to herein, can include any suitable hardware (e.g., a processor, an embedded controller, or an application-specific integrated circuit, among others), software (e.g., an application, among others), firmware, or any suitable combination of hardware, software, and firmware, in various aspects. Various aspects can be combined to include two or more of the aspects described herein.

According to an aspect, a computer-implemented method de-identifies data received from microphones. The method includes receiving data from one or more microphones and de-identifying the data. The de-identifying includes inputting the data into a machine learning system that has been trained to detect patterns in the data that are likely to identify a specific entity, and to remove the detected patterns from the data to generate de-identified data. An output from the machine learning system is received, where the output includes the de-identified data. According to some aspects, the microphones can be located in an operating room.

According to an aspect, the method can include one or both of training and retraining the machine learning system.

According to an aspect, the method can include where the received data is in an audio format, and the method can further include converting the received data into a discrete format and inputting the data in the discrete format into the machine learning system.

According to an aspect, the method can include where the de-identified data is in a text format.

According to an aspect, the method can include converting the de-identified data into an audio format.

According to an aspect, the method can include where the specific entity is a person.

According to an aspect, the method can include where at least one of the patterns includes a phrase that is associated with the person.

According to an aspect, the method can include where at least one of the patterns identifies a group that includes two or more entities.

According to an aspect, the method can include where the one or more microphones are located in an operating room.

According to an aspect, the method can include providing the de-identified data to a second machine learning system including one or more machine learning models that are trained to identify a plurality of surgical phases in a video of a surgical procedure.

According to an aspect, a computer program product includes a memory device having computer executable instructions stored thereon, which when executed by one or more processors cause the one or more processors to perform operations including receiving labeled training data comprising a plurality of sets of phrases, each set of phrases including a phrase and a corresponding de-identified phrase. The operations also include generating, using the labeled training data, a machine learning model to detect patterns in input data that are likely to identify a specific entity and to remove the detected patterns from the data.

According to an aspect, the computer program product can include where the generating the machine learning model is further based at least in part on a list comprising identifying phrases that each identify one or more entities.

According to an aspect, the computer program product can include where the operations further comprise retraining the machine learning model.

According to an aspect, the computer program product can include where the operations further include validating the machine learning model.

According to an aspect, the computer program product can include where the input data is received from one or more microphones located in an operating room.

According to an aspect, the computer program product can include where the operations further include receiving data from one or more microphones, de-identifying the data, the de-identifying comprising inputting the data into the machine learning model, and receiving an output from the machine learning system, the output including the de-identified data.

According to another aspect, a system includes a data collection system configured to capture a video of a surgical procedure, the video including data received from one or more microphones. The system also includes a machine learning execution system configured to execute one or more machine-learning models to identify a plurality of surgical phases in the video and to de-identify the data received from the one or more microphones. The system further includes an output generator configured to store the video with the surgical phases identified and the de-identified data.

According to an aspect, the system can include where the data from the one or more microphones is converted into a text format prior to being input to the model learning execution system and the de-identified data is in the text format.

According to an aspect, the system can include where the de-identifying of the data comprises removing any patterns in the data that are likely to identify a specific entity.

According to an aspect, the system can include where the de-identified data is in an audio format.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. The wireless network(s) can include, but is not limited to fifth generation (5G) and sixth generation (6G) protocols and connections. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source-code or object code written in any combination of one or more programming languages, including an object-oriented programming language such as Smalltalk, C++, high-level languages such as Python, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer-readable program instruction by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to aspects of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other devices to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the present invention. In this regard, each block in the flowchart or block diagrams may represent a module, segment, or portion of instructions, which comprises one or more executable instructions for implementing the specified logical function (s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects of the present invention have been presented for purposes of illustration but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects described herein.

Various aspects of the invention are described herein with reference to the related drawings. Alternative aspects of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains," or "containing," or any other variation thereof are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any aspect or design described herein as "exemplary" is not necessarily to be construed as preferred or advantageous over other aspects or designs. The terms "at least one" and "one or more" may be understood to include any integer number greater than or equal to one, i.e., one, two, three, four, etc. The terms "a plurality" may be understood to include any integer number greater than or equal to two, i.e., two, three, four, five, etc. The term "connection" may include both an indirect "connection" and a direct "connection."

The terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), graphics processing units (GPUs), general-purpose microprocessors, application-specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A computer-implemented method comprising:
receiving data, at a computing system, from one or more microphones in an operating room;
de-identifying the data by the computing system, the de-identifying comprising:
inputting the data into a machine learning system that has been trained to detect patterns in the data that are likely to identify a specific entity, and executing a de-identification inference engine to remove the detected patterns from the data to generate de-identified data comprising a transformation of one or more phrases in the data based on a combination of keywords and actions defined for a surgical environment;
receiving an output from the machine learning system, the output including the de-identified data; and
providing the output to a data collection system.

2. The method of claim 1, further comprising one or both of training and retraining the machine learning system.

3. The method of claim 1, wherein the received data is in an audio format and the method further comprises:
converting the received data into a discrete format; and
inputting the data in the discrete format into the machine learning system.

4. The method of claim 1, wherein the de-identified data is in a text format.

5. The method of claim 4, further comprising converting the de-identified data into an audio format.

6. The method of claim 1, wherein the specific entity is a person.

7. The method of claim 6, wherein at least one of the patterns includes a phrase that is associated with the person.

8. The method of claim 1, wherein at least one of the patterns identifies a group that includes two or more entities.

9. The method of claim 1, further comprising providing the de-identified data to a second machine learning system comprising one or more machine learning models that are trained to identify a plurality of surgical phases in a video of a surgical procedure.

10. A computer program product comprising a memory device having computer executable instructions stored in a non-transitory form thereon, which when executed by one or more processors cause the one or more processors to perform operations comprising:
receiving labeled training data comprising a plurality of sets of phrases, each set of phrases comprising a phrase and a corresponding de-identified phrase; and
generating, using the labeled training data, a machine learning model to detect patterns in input data that are likely to identify a specific entity and to remove the detected patterns from the data as a transformation of one or more phrases in the data based on a combination of keywords and actions defined for a surgical environment.

11. The computer program product of claim 10, wherein the generating the machine learning model is further based at least in part on a list comprising identifying phrases that each identify one or more entities.

12. The computer program product of claim 10, wherein the operations further comprise retraining the machine learning model.

13. The computer program product of claim 10, wherein the operations further comprise validating the machine learning model.

14. The computer program product of claim 10, wherein the input data is received from one or more microphones located in an operating room.

15. The computer program product of claim 10, wherein the operations further comprise:
receiving data from one or more microphones;
de-identifying the data, the de-identifying comprising inputting the data into the machine learning model; and
receiving an output from the machine learning system, the output including the de-identified data.

16. A system comprising:
a data collection system comprising one or more storage devices configured to capture a video of a surgical procedure, the video including data received from one or more microphones in an operating room;
a machine learning execution system configured to execute one or more machine-learning models on a processing system to identify a plurality of surgical phases in the video and to de-identify the data received from the one or more microphones by performing a transformation of one or more phrases in the data based on a combination of keywords and actions defined for a surgical environment; and
an output generator configured to store the video with the surgical phases identified and the de-identified data.

17. The system of claim 16, wherein the data from the one or more microphones is converted into a text format prior to being input to the model learning execution system and the de-identified data is in the text format.

18. The system of claim 16, wherein the de-identifying of the data comprises removing any patterns in the data that are likely to identify a specific entity.

19. The system of claim 16, wherein the de-identified data is in an audio format.

* * * * *